United States Patent [19]

Swett et al.

[11] 4,014,997
[45] Mar. 29, 1977

[54] ACYLPHOSPHONATE ESTERS
[75] Inventors: Leo Ralph Swett, Waukegan, Ill.;
Robert George Stein, Kenosha, Wis.;
George William Carter, Libertyville, Ill.
[73] Assignee: Abbott Laboratories, North Chicago, Ill.
[22] Filed: Oct. 31, 1975
[21] Appl. No.: 627,561
[52] U.S. Cl. .................. 424/200; 260/326.13 A; 260/941; 424/212
[51] Int. Cl.$^2$ ............... A01N 9/36; C07D 209/04; C07F 9/40
[58] Field of Search ............ 260/326.13 A, 941; 424/200, 212

[56] References Cited
UNITED STATES PATENTS
3,382,060   5/1968   Gier ..................... 260/941

*Primary Examiner*—Anton H. Sutto
*Attorney, Agent, or Firm*—Paul D. Burgauer; Robert L. Niblack

[57] ABSTRACT

A series of acylphosphonate esters have been found which prevent or relieve some of the ill effects of UV exposure to human skin.

7 Claims, No Drawings

ACYLPHOSPHONATE ESTERS

DETAILED DESCRIPTION

In the past, numerous drugs have been used as anti-inflammatories; some were used in oral therapy and others were applied topically to inflamed areas of the human skin.

The present invention is directed to new compounds, which are derived from certain compounds known to have antiinflammatory properties. More specifically, this invention is directed to compounds of the formula

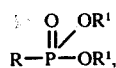

wherein $R^1$ is a lower alkyl radical and wherein R is an acyl moiety of a known organic, pharmaceutically acceptable acid having antiinflammatory properties. These new compounds are phosphonate esters in which the anti-inflammatory moiety is preferably attached in the enol form.

The term "organic, pharmaceutically acceptable acid, having anti-inflammatory properties" describes a small but definite class of compounds well known in the medical profession. They include such compounds as indomethacin, acetylsalicylic acid, 4-isobutylphenyl-acetic acid, 2-(4-isobutylphenyl)-propionic acid, 4-allyloxy-3-chlorophenyl-acetic acid, 2-(6-methoxynaphthyl)-propionic acid, 1-methyl-5-(4-toluyl)-pyrrol-2-acetic acid, 2-(3-benzoylphenyl)-propionic acid, 2-(3-phenoxyphenyl)-propionic acid and the like. When these compounds are converted to the above identified phosphonate esters, they tautomerize to a major extend into the enol form. The term "lower alkyl" is intended to include linear and branched alkyl radicals with 1 to 7 carbon atoms; however, the use of methyl and ethyl in place of $R^1$ is often preferred due to their cost advantage.

In general, the new compounds are prepared simply by reacting a trialkyl phosphite in a molar excess of 10 to 20% with the acid chloride of a pharmaceutically acceptable organic acid having anti-inflammatory properties, using a suitable medium for the reaction and stirring. Preferably, the solvent is carefully dried beforehand to assure exclusion of water. A suitable solvent is diethyl ether or a combination thereof with methylene chloride. After stirring for several hours, the precipitated condensation product is separated and recrystallized from a suitable solvent. Yields are generally in the range of 70 to 90% of theory.

The new compounds show anti-inflammatory properties similar to those of the parent compounds from which they are made. They can be used topically, by incorporating them into a bland ointment base of standard components, or they can be incorporated into an oral dosage form for ingestion. When used as tablets, the esters of the present invention show essentially the same anti-inflammatory properties as the parent compounds from which they are made. In some instances, the new compounds show less propensity for producing gastric irritation than the "parent" compounds from which they are derived.

When used in the form of ointments, a common ointment base may be used to disperse therein between 0.5 and 5% by weight of the new ester. Larger amounts may be used, but usually no need arises for increasing the concentration within the ointment of above 5% of active material; amounts of less than 0.5% may be used, if desired, but ordinarily, 0.5% by weight produces an excellent, homogeneous product. Ointments of this type can be used to protect the skin from ultra-violet light erythema or sunburns, or the ointment can be used subsequent to the occurrence of an arythema to reduce the inflammation or redness.

It will be apparent to those skilled in the art that in place of ointments, the above esters can also be incorporated into an oil base liquid for topical application to the skin to prevent or relieve some of the effects of sunburns. Such compositions, preferably contain between 1 and 10% by weight of the active ester, together with suspending agents, wetting agents and the like.

The above esters can easily be processed into dosage unit forms for oral ingestion. For instance, pharmaceutical tablets can be prepared by mixing the described ester, with the usual type of adjuvants, flavoring agents, fillers, buffers and/or coloring agents which together with a lubricant can be compressed into the usual tablets. Also a mixture of the above active compound with fillers and/or buffers or solid diluents can be processed into wafers, pills, or just simply filled into gelatin capsules in dosage units of suitable amounts. Preferably, a dosage unit contains between 30 and 1000 mg. of the active ingredient, and if desired, other drugs can be admixed therewith.

Oral dosage forms of the type indicated above do not require any coating for the purpose of taste masking or protection against the acid environment of the stomach. The active ingredient is of very low acid and water solubility so that the taste requires no or little masking and stomach irritation is almost totally absent. The active ingredient is lipid soluble and as such penetrates the cell membranes and will be found in the blood stream at sufficiently high doses to provide anti-inflammatory effects.

As briefly mentioned above, specific members of these phosphonate esters have advantages over the compounds used by the prior art, namely the known anti-inflammatories which are incorporated into the esters of this invention. These advantages primarily comprise the almost total absence of lesions observed in experimental animals which suggests substantial absence of any type of irritation in the gastro-intestinal tract in mammals. This is of particular interest because anti-inflammatories frequently have to be given on a permanent or semi-permanent basis which in the past have often led to serious damages to the gastro-intestinal tract of the patient, causing irritation or intestinal bleedings as well as activating ulcers.

In order to illustrate the method for preparing and using the new phosphonate esters, reference is made to the following examples which, however, are not meant to limit the invention in any way. In all instances, the syntheses lead to compounds of which the chemical analyses and absorption spectra were in conformance with the compounds of the desired structure.

EXAMPLE 1

A mixture of 92.8 g (0.409 mole) of 4-allyloxy-3-chlorophenyl acetic acid and 105 g (0.88 mole) of thionyl chloride in 400 ml of dry methylene chloride is stirred at room temperature for 48 hrs. and subsequently refluxed for 3½ hrs. The solvent and excess thionyl chloride is then removed on a rotating evaporator under reduced pressure from a warm water bath. The oil residue is redissolved in fresh solvent and evacuated again. The obtained 4-allyloxy-3-chlorophenyl acetyl chloride is distilled, resulting in a pure distillate of above 80% yield.

A solution of 8 g (0.0326 mole) of this chloride in 100 ml of dry ether is treated with 5.64 g (0.034 mole) of triethyl phosphite dissolved in 10 ml of dry ether in a rapid, drop-wise manner with stirring while dry nitrogen is bubbled through the mixture. The product, 4-allyloxy-3-chlorophenyl acetyl diethyl phosphonate precipitates from the mixture as a white solid after about 1 hour. The product is collected and dried; it melts at 130°–132° C and is obtained in a yield of 86% of theory.

EXAMPLE 2

In the manner described in the second paragraph of Example 1, 8 g of the acid chloride and 4.2 g of methyl phosphite are combined to result in a 70% yield of 4-allyloxy-3-chloro-phenylacetyl dimethyl phosphonate, melting at 110°–15° C.

EXAMPLE 3

In the manner described in Example 2, the corresponding diisopropyl-phosphonate ester is obtained in a yield of 70%; it melts at 123°–5° C.

EXAMPLE 4

A mixture of 45 g (0.125 mole) of indomethacin and 72 g (.605 mole) of thionyl chloride in 1 l. of dry benzene containing 2 drops of dimethylformamide is refluxed gently for 12 hours. The solvent and excess thionyl chloride is then removed on a rotating evaporator under reduced pressure from a warm water bath. The solid residue is triturated with dry benzene and again evacuated to dryness. The solid residue is dissolved in 150 ml of dry methylene chloride by warming the mixture on a steam bath; the mixture is then diluted with 1 l. of dry ether to which solution is added 18.6 g (0.15 mole) of trimethyl phosphite dissolved in 50 ml of dry ether in a rapid, drop-wise manner with stirring and while nitrogen bubbles through the mixture. After about 10–15 minutes, the product begins to crystallize out of the solution, and after 15 hours of stirring at room temperature, the yellow indomethacinoyl dimethyl phosphonate ester is collected, washed with ether/methylene chloride 10:1 and dried. The yield is 57% of theory, with the product melting at 150°–3° C being pure enough for use.

EXAMPLE 5

The above indomethacinoyl chloride obtained as shown in Example 4 is treated with a 20% excess of tributyl phosphite in dry methylene chloride/ether 1:3. The product is isolated from the reaction mixture by concentrating and addition of dry pentane. The pale yellow solid is recrystallized from benzene/petroleum ether in a yield of 31% of theory for indomethacinoyl di-n-butyl phosphonate ester melting at 104°–6° C.

EXAMPLE 6

In the manner described above, 2-(6-methoxy-naphthyl)propionic acid is converted to the corresponding propionyl chloride, which is then converted, as shown in the above Examples, to the corresponding dimethyl phosphonate ester.

EXAMPLE 7

Similarly to the above, acetyl salicylic chloride is reacted with trimethyl phosphite, triethyl phosphite or tributyl phosphite to yield a) acetyl salicyloyl dimethyl phosphonate, b) acetoyl salicyloyl diethyl phosphonate, and c) acetoyl salicyloyl di-n-butyl phosphonate, respectively.

EXAMPLE 8

Guinea pigs (8 animals per group) were exposed to ultraviolet radiation to produce erythema. At various intervals thereafter, the various groups of animals were treated with a Pramme cream containing 0.5 weight % of the compound of Example 4 at a level of 10 mg of cream per 100 mm$^2$ area on the dorsal surface. The average degree of blanching for the first group medicated 30 min. after exposure was 2.8 (scale of 0–3 with 3 meaning complete blanching back to skin color), the second and third groups, treated after 1 hr. and 2 hrs., respectively, showed 2.6, and the group treated after 4 hrs. showed a rating of 2.5.

EXAMPLE 9

In an experiment similar to that in Example 8, blanching was evaluated 4 hrs. after exposure with the cream medication being applied 15 min. after exposure. There were 8 guinea pigs in the group and the test was to establish the medication dosage (% wt/wt concentration per 10 mg of cream) required to produce visible blanching in 4 animals ($ED_{50}$). With the compound of Example 4, an $ED_{50}$ of 0.045 was determined.

EXAMPLE 10

Oral activity of the compounds described above was established by administering the drug by gavage to fasted rats in accordance with the procedure of Winter et al in Proc. Soc. Exp. Bio. Med, 1962, Vol. III, p. 544. The figures given below show the reduction in edema volume on the rat paw:

| Compound | Dose | | Reduction |
|---|---|---|---|
| Ex. 1 | 10 | mg/kg | 10% |
| Ex. 1 | 20 | " | 34% |
| Ex. 2 | 30 | " | 42% |
| Ex. 4 (enol) | 2.5 | " | 28.7% |
| Ex. 4 (keto) | 2.5 | " | 15.3% |
| Ex. 5 | 6 | " | 28% |
| Ex. 6 | 25 | " | 20% |
| Ex. 7a | 200 | " | 24% |

Each of the compounds was given to groups of 6 animals as a 0.2–1.0% suspension in 0.5% aqueous methylcellulose, with the drug concentration varying with the amount of drug required.

When the above test drugs are administered as dry powders in a gelatin capsule, substantially identical results as those reported above are observed.

In order to make other dosage forms, the above esters are granulated in the usual fashion with 1–5 times their weight in starch. After sifting, the granules are combined with smaller amounts of lubricants, flavoring agents and coloring agents and, if desired, pharmaceutically acceptable fillers such as additional portions of corn starch. After uniformly blending these ingredients, they are compressed into tablets of 100, 250, or 500 mg drug per tablet in a standard tableting machine. These tablets may be coated in the usual fashion, although coating is strictly a matter of choice as these tablets do not require protection or taste masking.

What is claimed is:

1. The acylphosphonate ester of the formula

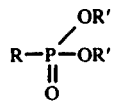

wherein R' is a lower alkyl radical and wherein R is an acyl moiety of an organic, pharmaceutically acceptable acid having anti-inflammatory properties.

2. A composition in the form of an ointment for alleviating the symptoms of inflammation of the skin in warm-blooded animals containing a pharmaceutically acceptable ointment base and dispersed therein, between 0.5 and 5% by weight of the acylphosphonate ester of claim 1.

3. The compound of claim 1, wherein R is indomethacinoyl, acetylsalicoyl, 2-(6-methoxynaphthyl)-propionyl or 4-allyloxy-3-chlorophenyl-acetyl.

4. The ester of claim 1, wherein R is indomethacinoyl and R' is methyl or ethyl.

5. The ester of claim 1, wherein R is acetylsalicoyl and R' is methyl or ethyl.

6. The ester of claim 1, wherein R is 2-(6-methoxynaphthyl)-propionyl and R' is methyl or ethyl.

7. The ester of claim 1, wherein R is 4-allyloxy-3-chlorophenylacetyl and R' is methyl or ethyl.

* * * * *